(12) United States Patent
Alexander

(10) Patent No.: US 6,283,974 B1
(45) Date of Patent: Sep. 4, 2001

(54) SURGICAL TIP FOR PHACOEMULSIFICATION

(76) Inventor: Aaron James Alexander, 2202 SW. 112th St., Gainesville, FL (US) 32607-1126

( * ) Notice: Subject to any disclaimer, the term of this patent is extended or adjusted under 35 U.S.C. 154(b) by 0 days.

(21) Appl. No.: 08/971,052

(22) Filed: Nov. 14, 1997

(51) Int. Cl.$^7$ .................................................. A61F 09/00
(52) U.S. Cl. ............................ 606/107; 606/169; 604/22
(58) Field of Search .................... 606/107, 169, 606/167, 170, 2; 604/19, 22

(56) References Cited

U.S. PATENT DOCUMENTS

| | | |
|---|---|---|
| D. 266,872 | 11/1982 | Anderson . |
| D. 357,313 | 4/1995 | Wortrich . |
| 884,761 | 4/1908 | Richard . |
| 1,881,415 | 10/1932 | Tingleff . |
| 3,175,554 | 3/1965 | Stewart . |
| 3,589,363 | 6/1971 | Banko . |
| 4,689,040 | 8/1987 | Thompson .............................. 604/22 |
| 4,816,018 * | 3/1989 | Parisi ..................................... 604/22 |
| 4,869,715 | 9/1989 | Sherburne .............................. 604/22 |
| 4,959,049 | 9/1990 | Smirmaul ............................... 604/22 |
| 5,199,943 * | 4/1993 | Wypych ................................ 606/169 |
| 5,213,569 | 5/1993 | Davis ..................................... 604/22 |
| 5,417,654 | 5/1995 | Kelman .................................. 604/22 |
| 5,464,389 * | 11/1995 | Stahl ..................................... 606/169 |
| 5,520,633 | 5/1996 | Costin .................................... 604/22 |

(List continued on next page.)

OTHER PUBLICATIONS

"Today, It's Amazing What You Can Get In A Micro–Incision Needle", Storz Ophthalmics, Apr., 1996.

Zabel, Karen "MicroTip increases visibility", Ophthalmology Times, Sep. 1, 1996, p. 30.

"High–Vacuum Less Ultrasound Used", Ophthalmology Times, Sep. 1, 1996, p. 46.

Kumar, Y.; Kumar. A;, Kumar, B. "Effect on ultrasound propagation in metal rods due to contact with liquid", Acustica—Acta Acustica, vol. 83, No. 1, p. 78–81, Abstract No. A9712–4335–002.

Campos–Pozuelo, C; Gallego–Juarez, J.A., "Limiting strain of metals subjected to high–intensity ultrasound", Acustica—Acta Acustica, vol. 82, No. 6, p. 823–8, Abstract No. A9704–4325–005.

Cocker, R.P.; Challis, R.E., "A study of ultrasonic wave propagation through parallel arrays of immersed tubes", Journal of Sound and Vibration, vol. 193, No. 5, p., 1049–68, Abstract No. A9616–4340–003.

Lipner, Maxine, "New phaco needle maximizes control during procedure", Ocular Surgery News, Apr. 1, 1996 (Web Home Page printed Aug. 5, 1997).

(List continued on next page.)

*Primary Examiner*—Glenn K. Dawson
(74) *Attorney, Agent, or Firm*—Saliwanchik, Lloyd & Saliwanchik

(57) ABSTRACT

A micro surgical phacoemulsification tip wherein a repetitive pattern is etched into the inner lumen surface of a surgical tip in a controlled pattern such that a resonance condition is created which is in harmonic phase with the frequency of the phacoemulsification energy source, thereby reducing destructive interference waves and creating constructive waves; virtually eliminating instantaneous tip temperature spikes and removing the risk of potential tissue burning. More specifically, the present invention is drawn to phacoemulsification needles having a lumen surface having micro-grooved channels positioned thereon which center harmonic phased ultrasonic generated acoustic wavefront interiorly from the needle wall. The micro-grooved channeling of the present invention will work with the axial length of any phacoemulsification needle tip harmonic.

12 Claims, 17 Drawing Sheets

U.S. PATENT DOCUMENTS

| | | | |
|---|---|---|---|
| 5,562,609 | 10/1996 | Brumbach | 604/22 |
| 5,580,347 | 12/1996 | Reimels | 604/30 |
| 5,591,127 | 1/1997 | Barwick, Jr. et al. | 604/66 |
| 5,653,724 | 8/1997 | Imonti | 606/169 |
| 5,935,096 * | 8/1999 | Barret | 604/22 |
| 5,993,408 * | 11/1999 | Zaleski | 604/22 |
| 6,007,555 * | 12/1999 | Devine | 604/22 |
| 6,074,396 * | 6/2000 | Geuder | 604/22 |

OTHER PUBLICATIONS

Singer, Jack A.; Fine, I. Howard, "Diamond–shaped tip improves phaco auto–crack technique", Ophthalmology Times, vol. 22, No. 18, p. 14–15, Sep. 15,1997.

Zabel, Karen "Low ultrasonic energy can create good phaco", Ophthalmology Times; vol. 22, No. 11, p. 7, 38–39, Jun. 1, 1997.

We Designed It. Now, The Fine–Tuning Is Up To You., AMO Diplomax–OCS Phaco Technology.

Guttman, Cheryl "Smaller tip yields multiple enhancements for phaco", Ophthalmology Times, vol. 22, No. 10, p. 35, May 15, 1997.

Fine, Howard I. "Update on Phaco Machines", Review of Ophthalmology, Jun. 1996.

Fine, Howard I. "The Continuing Evolution of Phaco", Eyecare Technology, p. 1–5, Apr. 1996.

* cited by examiner

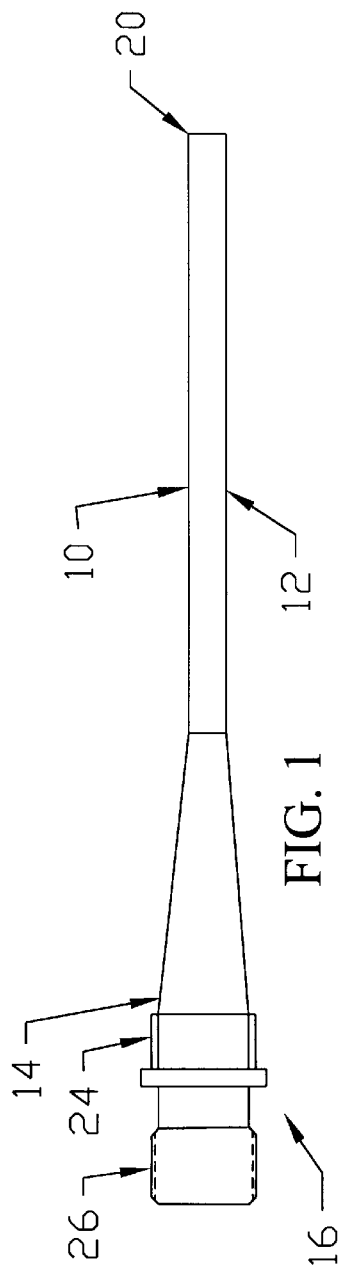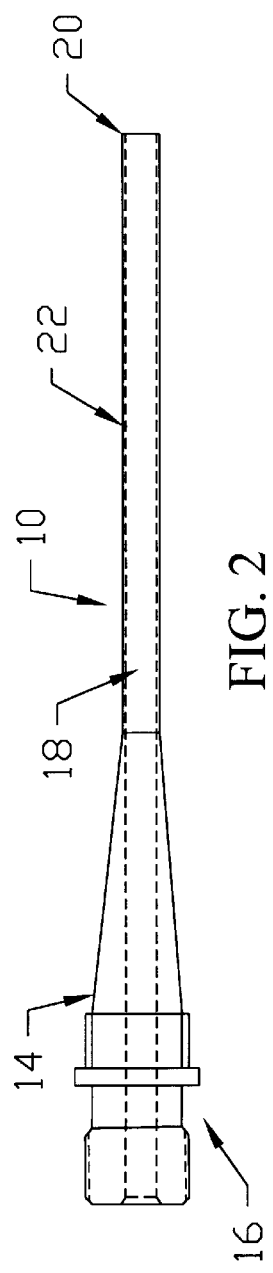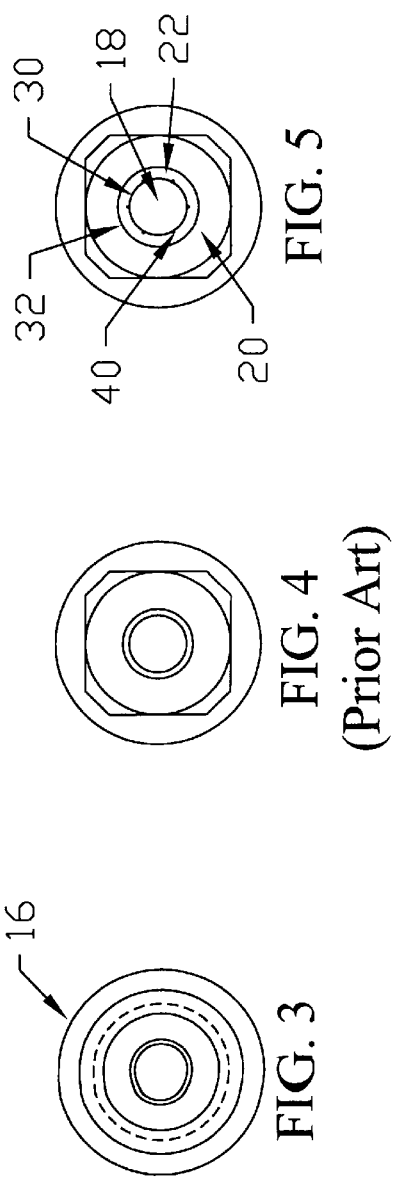

60.0000°

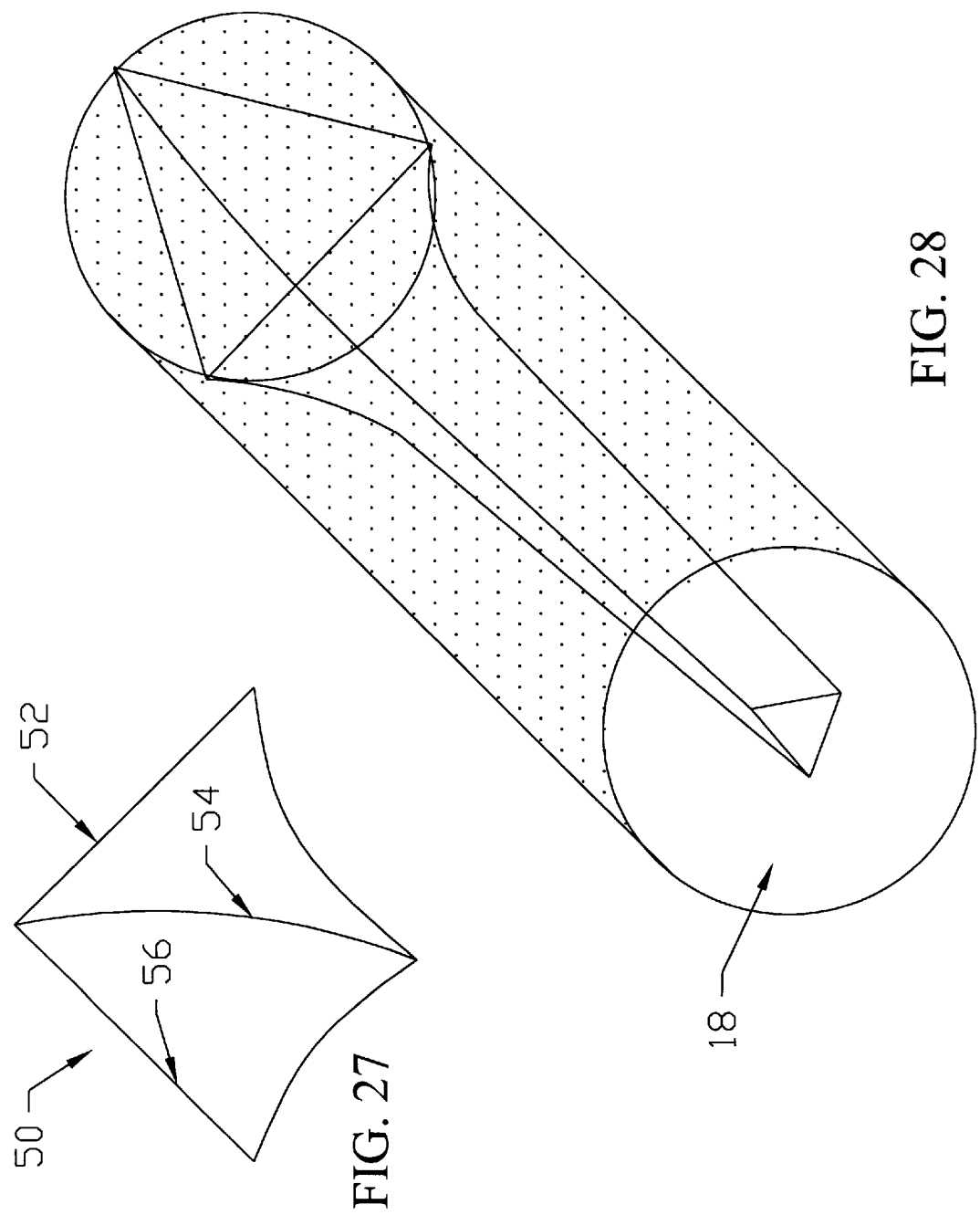

SURGICAL TIP FOR PHACOEMULSIFICATION

BACKGROUND OF THE INVENTION

1. Field of the Invention

This invention relates to tissue removal in a liquid environment and, more particularly, an improved surgical tip for cutting, aspirating and removing desired tissue by utilization of ultrasonic frequencies with minimal or reduced incidences of temperature increases along the axial length of the surgical tip.

2. Description of the Background Art

"Phacoemulsification" traditionally has referred to a method of treating cataracts of the lens of the eye whereby an ultrasonic device (consisting of a specific frequency generator, vacuum pump, handpiece, and cannula) is utilized to disintegrate the cataract, which is then aspirated and removed. A cataract is calcified tissue protein of the lens of the eye, its capsule, or both. An estimated 1.25 million people worldwide are blinded by cataracts each year. Traditionally, surgical removal of the lens is required. In the past, this procedure required an incision (post limbus scleral) large enough to permit extraction of the lens and implantation of an artificial lens. Now the procedure can be done through a very small (2–3 mm), suture-less incision of the clear cornea with less complications and much shorter healing times. Ultrasound energy generating sonic shockwaves, a wavefront or imploding microbubbles is used to fragment the cataract, which can then be aspirated and removed through the incision. This technique and method for extracting the lens cortex was originally described in U.S. Pat. No. 3,589,363 to Banko et al, the disclosure of which is incorporated herein by reference.

After extraction of the cataract, a replacement lens is then folded with forceps or an injector and inserted through the small incision. Over the last decade, phacoemulsification has become the generally accepted mode of cataract removal for the majority of ophthalmic surgeons.

Traditionally, phacoemulsification surgical instruments are used for the disintegration of diseased tissue of the eye, and in particular, the opaque hardened protein of the lens (cataract) of the eye. During phacoemulsification, high frequency ultrasound energy, which travels as sonic shock waves or a sonic "wavefront", ranging from approximately 5 to 70 kilohertz (kHz) is delivered to the eye via a hand held transducer that conveys the acoustic wavefront energy into the eye via a thin walled needle or cannula tip threaded to the handpiece. More specifically, ultrasound energy is generated by piezoelectric crystals or magnetostrictive elements which are aligned within a surgical handpiece and delivered through an energy transferring surgical tip.

In conjunction with the ultrasound energy, a surgical console includes a variable speed peristaltic pump thereby producing vacuum to the handpiece. Additionally, an irrigation fluid source is fluidly coupled to the phacoemulsification handpiece whereby aspiration fluid of a sterile solution is circulated around the surgical tip through a silicone sleeve that encompasses the outer diameter of the surgical tip.

During phacoemulsification, the ultrasonic probe or surgical tip is inserted into the eye through a small incision. The surgical tip has several functions: it vibrates at ultrasonic frequencies and it aspirates fluid and particles from the eye. The ultrasound energy vibrates microbubbles (somnulance) that implode and collapse which disintegrate the lens nucleus and the surgical tip aspirates the nuclear particles away. In order to maintain the stability or pressure within the eye, vasoelastic material (hyaluronic acid) is injected into the anterior chamber to maintain corneal stability. Irrigation fluid composed of a balanced salt solution is infused around the vibrating surgical tip via a sleeve to cool the tip and aid in flushing out the pulverized tissue matter.

The advantages of phacoemulsification stem from the surgeon's ability to operate with a smaller incision than is required for conventional cataract surgery. A smaller opening in the eye means better control over fluid pressure within the eye (chamber stability), a more rapid recovery of wound site incision, less surgery-induced astigmatism and almost immediate return of visual activity.

Recently, the general principles underlying phacoemulsification have begun to be applied to other surgical disciplines. For instance, Mentor O & O of Norwell, MA manufactures both cataract and liposuction phacoemulsification instrumentation. Liposuction is the removal of subcutaneous fat tissue with a blunt tip cannula introduced into the fatty area through a small incision. Suction is then applied and fat tissue removed. Liposuction is a form of plastic surgery intended to remove adipose tissue from localized areas of fat accumulation as on the hips, knees, buttocks, thighs, face, arms, or neck.

Despite the advantages of phacoemulsification over more invasive techniques of cataract treatment, the phacoemulsification procedure can result in complications such as non-vascular tissue burns and damage, endothelial cell loss which is critical for the endothelium pump mechanism feeding the cornea. More specifically, the inherent safety problems with phacoemulsification during microsurgery are 1) needle tip temperature spikes during occlusion which can lead to cornea tissue burns; 2) possible rupture of the eye lens capsular bag (posteriorly) due to needle proximity, ultrasound power or vacuum; 3) degradation, disruption or removal of structurally critical corneal endothelium cells; and 4) lens epithelial cells left behind in the capsular bag due to dispersion during phacoemulsification and attendant vacuuming of tissue during microsurgery. For instance, hard nuclei blockage of the surgical tip may occur during phacoemulsification that results in a stoppage of fluidics and accompanying spike in the tip temperature which may cause burning and damage to the cornea at the port site. Any burning or damage to the cornea can result in complications at the wound site.

Continuing efforts are being made to improve eye surgery methods and apparatus. Advances have been made to circumvent the problems associated with phacoemulsification both in the technical (i.e. "hardware") and technique aspect of the phacoemulsification surgery. Consider the large number of background patents that reference U.S. Pat. No. 3,589,363 to Banko et al. and teach cataract surgery techniques or apparatus.

In addition, apparatus for controlling the parameters of a phacoemulsification handpiece via the phaco machine are disclosed in another large number of patents. By way of example, note U.S. Pat. No. 5,591,127 to Barwick, Jr. et al.; U.S. Pat. No. 5,580,347 to Reimels and U.S. Pat. No. 5,520,633 to Costin. Manufacturers have developed microprocessing systems which permit a surgeon to operate without concern of occlusion by sensing the rise in vacuum and shutting down ultrasound power. Phaco machines allow the surgeon to preset or vary the aspiration rate, vacuum and ultrasound power.

For instance, the AMO® DIPLOMAX™, manufactured by Allergan, Inc. of Irvine, Calif. is designed to protect against corneal burns and permits the surgeon to program "Occulsion Mode Phaco™", "Burst Mode Phaco™" and Autopulse Phaco™". With Burst Mode Phaco™ a surgeon may deliver ultrasound via a single controlled burst or in multiple controlled bursts of power. Additionally, with the Autopulse Phaco™ a surgeon may adjust between pulse mode and continuous power based upon the type of sculpting and the density of the cataract. These systems are designed to react in microseconds to reduce or shut down power before damage can occur. However, these systems are often cost prohibitive.

Alternatively, surgeons are working on improved techniques that require less ultrasound power. For instance, some surgeons are working supercapsularly to protect the delicate structures within the bag or working within a smaller area of "operation" (i.e. pulling the divided pieces of lens to the center of the tip). Still further, some surgeons are attempting to utilize higher working vacuum in an effort to reduce the amount of ultrasound power required.

Lastly, numerous patents are drawn to phacoemulsification needles. By way of example, note U.S. Pat. No. D357,313; U.S. Pat. No. 5,213,569 to Davis; U.S. Pat. No. 4,689,040 to Thompson; U.S. Pat. No. 4,959,049 to Smirmaul; U.S. Pat. No. 5,653,724 to Imonti; U.S. Pat. No. 5,417,654 and U.S. Pat. No. 4,869,715 to Sherburne. Additionally, many "improved" needles are being advertised in the industry.

TurboSonics®MicroTip™ needle reduces tip size to 0.9 mm form the standard tip size of 1.1 mm. Due to its smaller inner diameter, surgeons must accommodate by utilizing a smaller incision and a higher vacuum power.

The Storz® MicroFlow™ needle utilizes straight longitudinal channels defined in the outer surface or diameter of the needle, thereby giving the MicroFlow™ needle the appearance of a "fluted Greek column" to permit fluid to enter the eye unimpeded through a 2.5 mm incision. These longitudinal grooves resemble linear extrusions and do not converge.

Additionally, Surgical Design manufactures phacoemulsification needles that incorporate square or diamond shaped distal tips. Utilizing these tips a surgeon may perform auto-crack phaco wherein the nucleus is cracked without chopping it with a second instrument.

Efforts to improve eye surgery apparatus and techniques continue. Accordingly, it is an object of this invention to provide an improvement which overcomes the aforementioned inadequacies of the prior art devices and provides an improvement which is a significant contribution to the advancement of the art.

Another object of this invention is to utilize less phaco power thereby helping to preserve the corneal endothelium without reducing the efficiency of the phacoemulsification procedure.

It is a further object of this invention to provide a surgical tip which may be readily utilized with current commercially available phacoemulsification machines.

A further object of the present invention is to provide a surgical tip which is not effected by occlusion with lens material but works with the occlusion in a controlled manner.

A further object of the present invention is to provide a surgical tip which runs cooler thereby obviating the necessity to reduce the temperature of the sterile solution.

A further object of the present invention is to provide a surgical tip that virtually eliminates temperature spikes along the axial length of the surgical tip thereby protecting the non-vascular cornea tissue.

A further object of the present invention is to provide a surgical tip that facilities the ease of lens removal across the nucleus density spectrum.

A further object of the present invention is to provide a surgical tip having increased longevity.

A further object of the present invention is to provide an apparatus and method for producing micro-etching within a small bore lumen.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a micro surgical phacoemulsification tip wherein a repetitive pattern is etched into the inner lumen surface of a surgical tip in a controlled pattern such that a resonance condition is created which is in harmonic phase with the frequency of the phacoemulsification energy source, thereby reducing destructive interference waves and creating constructive waves; virtually eliminating instantaneous tip temperature spikes and removing the risk of potential tissue burning. More specifically, the present invention is drawn to phacoemulsification needles having a lumen surface having micro-grooved channels positioned thereon which center harmonic phased ultrasonic generated acoustic wavefront interiorly from the needle wall. The micro-grooved channeling of the present invention will work with the axial length of any phacoemulsification needle tip harmonic.

In a preferred embodiment, one complete revolution of the helix may occur on the lumen length from distal point to hub base. However, it should be well understood that any repetitive pattern may be utilized in the surgical tip of the present invention which is in harmonic phase with the ultrasonic source. The micro-channels create a resonance condition which is in phase with the piezoelectric crystals and wave carrier cannula instrument, thereby producing a focus of the wave wall energy at points of intersect that centers in the lumen and transfers less energy towards the peripheral wall. By utilizing the surgical tip of the present invention, phacoemulsification of the lens nuclei tissue is performed within the confines of the lumen as opposed to outside the lumen as occurs with previously known phacoemulsification needles. There is a conservation of transferred energy as the matter is proximally closer to the resultant shock wavefront. Therefore the corneal endothelium is preserved and less epithelial cells are likely to disperse and remain behind.

Since the surgical tip of the present invention focuses the ultrasound energy proximally within the lumen of the piezoelectric crystals, approximately fifty (50)% less energy is required as the wavefront boundary is not being dissipated by travel vectors away from the distal tip end and instead is being almost fully utilized at emittance peak levels and not being effected by transfer loss vectors.

Additionally, the orientation of the helical micro-channels advantageously increase fluidics consistently during occlusion of the tip with partial nuclei blockage, thereby eliminating the instantaneous tip temperature spike during such point in the procedure and the resulting risk of damage due to tissue burning at the limbus side of the cornea.

The invention of this patent application is further drawn to a micro-tool and method for scoring the inner diameter of a lumen.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a side view of the surgical tip of the present invention;

FIG. 2 is a cross-sectional view of the surgical tip as shown in FIG. 1;

FIG. 3 is an end elevational view thereof;

FIG. 4 is a distal end elevational view of a prior art tip;

FIG. 5 is a distal end elevational view of the surgical tip of the present invention;

FIG. 27 is elevational view of the micro-tool of the present invention;

FIG. 28 is a perspective view of a micro-tool for scoring a lumen wall with equilaterally opposed channels;

Similar reference characters refer to similar parts throughout the several views of the drawings.

DETAILED DESCRIPTION OF THE PREFERRED EMBODIMENT

Figure 8:
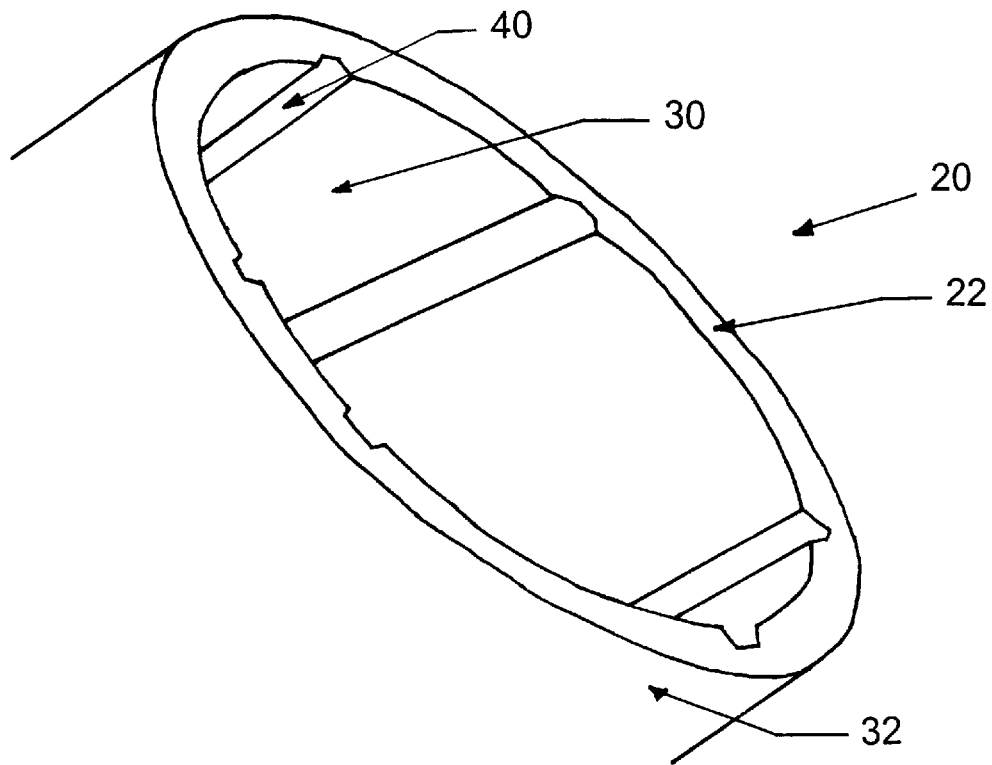
FIG. 8 is a perspective view of the phacoemulsification needle of the present invention shown at approximately ×100 power.

With reference to the drawings and in particular to FIGS. 5 and 8, a new and improved surgical tip embodying the principles and concepts of the present invention and generally designated by the reference number 10 will be described. For ease of discussion, the apparatus of the present invention shall be referred to herein as a surgical tip and generally refers to any phaco tip, cannula or needle that may be utilized in an ultrasound surgical procedure. A "cannula" can refer to any small tube that can be inserted into a body cavity, duct or vessel. Similarly, the term "needle" references a pointed instrument for stitching, ligaturing or puncturing.

It should be understood that the surgical tip of the present invention may be utilized in conjunction with any commercially available ultrasonic system for the disintegration and removal of tissue and in no way is limited to removal of cataracts.

A surgical tip embodying the principles and concepts of the present invention may either be manufactured in accordance with industry standards or alternatively any currently available phaco tip, needle or cannula may be modified in accordance with the present invention. The present detailed discussion is based upon a standard Alcon 20K phaco tip, manufactured by Alcon Laboratories Inc., Alcon Surgical Products Division of Fort Worth, Tex., which was modified in accordance with the present invention.

As illustrated in FIG. 1, the preferred embodiment of the surgical tip of the present invention 10 comprises an elongate hollow member 12 having a distal end 20 and a proximal end 14 wherein said distal end and said proximal end define an axial length. The surgical tip of the present invention further comprises a non-invasive, fastening means 16 designed to releasably attach said surgical tip to a handpiece (not shown) whereby ultrasonic frequencies are conveyed to said surgical tip. The fastening means may comprise any mechanical fastening elements known in the phacoemulsifcation art, including but not limited to a threaded portion 26 and hub 24 which facilitates the connection of the surgical tip to the phacoemulsification handpiece (not shown). The fastening means 16 is in fluid communication with the elongate hollow member 12 and phaco handpiece (not shown).

As illustrated in FIG. 2, the surgical tip 10 has defined therein a lumen 18 which runs coaxial the length of the surgical tip. Specifically, the surgical tip has an elongate hollow member 12 comprised of a thin wall 22 which encloses and defines a lumen 18. The elongate hollow member 12 further comprises a distal tip portion 20 and a proximal end 14 adjacent the fastening means 16 wherein said elongate hollow member is in fluid communication with a ultrasound source and the tissue to be emulsified. The wave front generated by the energy source travels through the lumen.

As illustrated in FIG. 8, the thin wall 22 of the elongate hollow member has an inner surface 30 and an outer surface 32. Additionally, as illustrated in FIGS. 2 and 6, the elongate hollow member has an inner diameter 15 and an outer diameter 17 with the lumen being defined by the inner surface diameter of the wall.

Generally speaking, phacoemulsification needles average 2.5 cm. in length with an outside wall diameter of approximately 0.030–1.0 mm, an inside wall diameter of approximately 0.25 to 0.75 mm and a wall thickness of approximately 0.0035 mm. Generally, as illustrated in FIG. 5, the cross-section of the elongate hollow member is circular in shape. However, the cross-section may also be elliptical or have a square or diamond shaped distal end.

Figure 6:
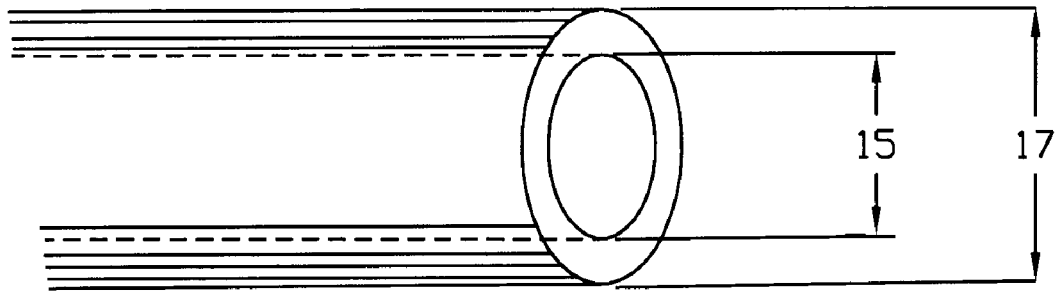
FIG. 6 a top view of a distal end of a prior art phacoemulsification tip.
Figure 7:
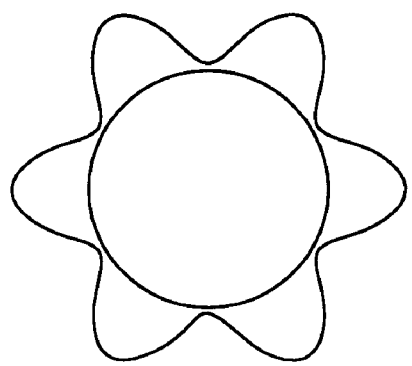
FIG. 7 is a distal end elevational view of a prior art tip having grooves defined in the outer diameter.

In conventional phacoemulsification needles, as illustrated in FIGS. 6 and 7, the inner surface diameter of the lumen wall is smooth.

In the context of liposuction procedures, liposuction-phacoemulsification cannula are available in three different sizes dependent on the body part and procedure. By way of example: size (1) is 12 cm in length with an inside diameter of 1.9 mm and outside diameter of 3 mm; size (2) may be 12, 24 or 35 cm in length with an inner diameter of 2.1 mm and an outside diameter of 4 mm; size (3) may be 24 or 35 cm in length with an inner diameter of 2.5 mm and an outer diameter of 5 mm. All of these cannulas preferably have two distal end holes which are oriented approximately 3 mm from the distal tip of the cannula which are drilled through the side wall of the cannula for aspiration of emulsified matter. Therefore, the silicon sleeve for continuous irrigation and cooling of the needle is optional.

In the phaco console to be produced by Mentor O & O Inc. the pizeoelectric crystals in the handpiece run at a 27 kHz constant setting.

The surgical tips of the present invention are preferably fabricated of a titanium compound and are manufactured in a similar manner as conventional phacoemulsification needles. Based upon Federal Drug Administration (F.D.A.) approval for implant capabilities and high quality resonance functioning, phacoemulsification surgical tips are standardly manufactured from a titanium alloy comprised of 90% titanium, 6% aluminum and 4% vanadium. However, any alloy known in the phacoemulsification art may be utilized to fabricate the surgical tip of the present invention.

The distal end of the surgical tip may be pitched either 0°, 15°, 30°, 45° or 60° depending on the preferred cutting angle.

Figure 9:
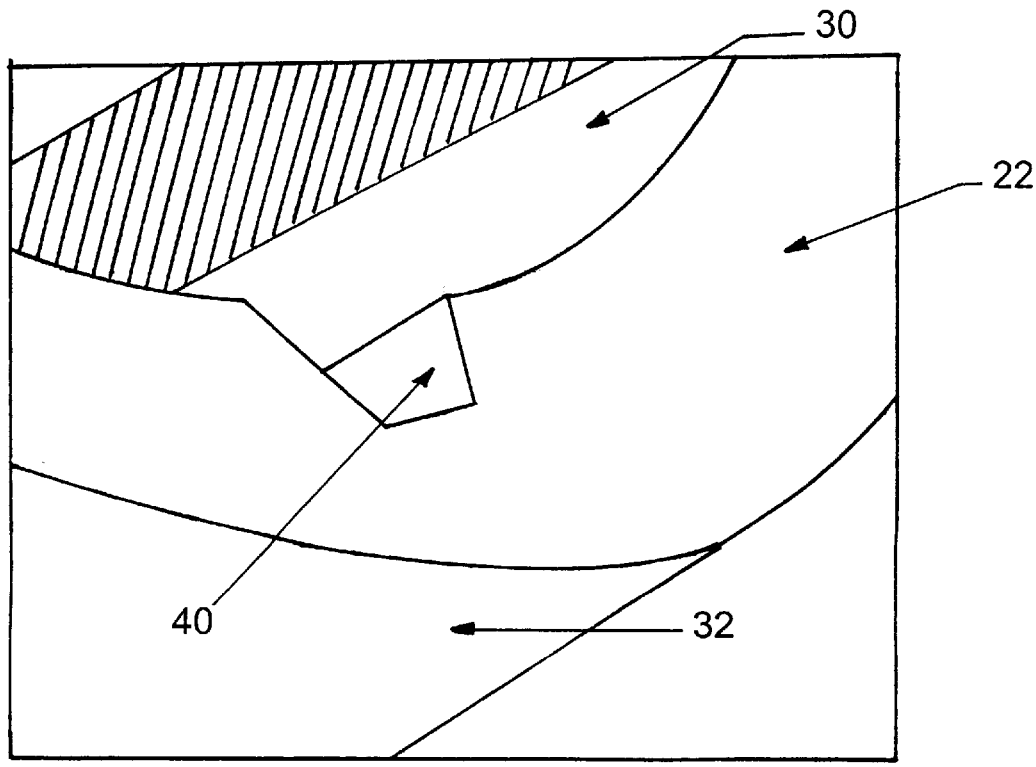
FIG. 9 is a detailed view of a micro-channel shown at approximately ×500 power.

As illustrated in FIGS. 5, 8 and 9, a major improvement of a controlled repetitive pattern on the surface of the lumen. More specifically, the surgical tip of the present invention is the inclusion of micro-channels 40 defined in the inner surface 30 of the elongate hollow member wall 22. These micro-channels 40 advantageously increase fluidics consistently during occlusion of the end with partial nuclei blockage, thereby aiding in eliminating the instantaneous distal tip temperature spike which may occur during aspiration. Additionally, multiple micro-channels aid in establishing a resonance condition that is in phase (constructive interference) with the ultrasonic energy source thereby focusing and centering the wave wall energy in the lumen and transferring less energy towards the peripheral wall thereby combating mechanical friction which may occur at the distal end. Lastly, when utilizing the surgical tip of the present invention, phacoemulsification is performed generally within the confines of the lumen as opposed to outside the lumen as occurs with prior art phaco tip needles. Therefore, the corneal endothelium is preserved and less epithelial cells are likely to disperse and remain behind causing future opacity.

In use, when the surgical tip is in fluid communication with said phacoemulsification handpiece, the elongate hollow member is surrounded by a tubular irrigation sleeve which forms a conduit (not shown). Irrigation fluid, which is usually a buffered saline solution, is introduced into the eye chamber through the conduit defined between the outer diameter of the elongate hollow member and the silicone irrigation sleeve. Any fluid or fragmented material is aspirated from the eye through the surgical tip lumen.

By way of background information, an ultrasonic transducer is a transducer that converts alternative-current energy above 5 kilohertz to mechanical vibrations of the same frequency or ultrasonic acoustic waves. The principles behind this energy conversion is well known by those skilled in the art. The transducer is generally either magnetostrictive or piezoelectric. Currently available phacoemulsification handpieces generate high frequency ultrasound energy ranging from approximately 10 kHz to 70 kilohertz (kHz). Generally speaking, currently available phacoemulsification tips are designed to operate within a predetermined kilohertz range. By way of example, the Alcon 20 K needle is set at approximately 39 kHz. Phacoemulsification tips are designed to cause cavitation within the lens and cortex. Such cavitation is useful for disintegrating the lens but generates a good deal of heat along the axial length of the tip and can be difficult to control. Additionally, any axial length random striations or manufacturing deformation on the distal end wall can lead to waveform energy interference, cannula inefficiency and heat build-up during use.

In use, the surgical tip is inserted into the eye through an incision that typically ranges from 1.9 mm–2.3 mm wherein it encounters the lens. Focusing specifically on the surgical tip, once the tip engages the lens nucleus a burst of ultrasonic vibration is applied to the tip for cutting or otherwise disintegrate the lens nucleus. Usually bursts of 0.50–2.0 seconds are used but sometimes-longer bursts may be used. In the cavitation mode, which traditionally occurs outside the lumen at the distal tip, the surgical tip cuts and breaks away a portion of lens material. This lens material then may be aspirated through the lumen of the surgical tip. Often, a tip temperature spike may occur caused by occlusion of the tip by dense eye lens nucleus tissue. Cornea tissue burns occur at approximately 52° C. (125.6° F.). The risk of corneal burn is compounded by the fact that cornea tissue is non-vascular. Traditionally, prior art phacoemulsification needles have not incorporated any patterning on the inner surface of the lumen wall to focus the ultrasound wavefront.

Attempts have been made to focus the acoustic wave energy generated by the hand held transducer. Specifically, U.S. Pat. No. 5, 213,569 to Davis, the disclosure of which is incorporated herein by reference, utilizes focusing surfaces at the distal end of phacoemulsification needles in an effort to focus the acoustic wave energy. However, while the phacoemulsification needle of Davis arguably focuses wave energy at the distal end of the phacoemulsification needle, the focusing surfaces of Davis are not specifically tuned to the ultrasound wavefront in an effort to reduce interference.

In the surgical tip of the present invention, micro-grooved channels are defined in the inner surface of the lumen wall which center harmonic phased ultrasonic generated acoustic waves or the "wavefront" interiorly from the needle wall. This improvement is based upon the premise that ultrasonic generated acoustic waves can be focused to work more efficiently and safely in removing calcified protein tissue from the anterior chamber of the eye. The invention of this application is the use of an etched repetitive pattern in the inner lumen surface to enhance the ability to reduce the amount of high frequency ultrasonic energy (i.e. micro bubbles) introduced into the delicate anterior chamber of the eye. In practice, the surgical tip of the present invention creates a "primary working stage" within the lumen of the surgical tip that is insulated and advantageously utilizes the surface area of the inner surface of the lumen wall to carry out phacoemulsification.

The increased surface area generating the micro bubbles work with the vacuum function and capabilities of the cannula and handpiece to simultaneously phaco and vacuum, thereby utilizing less time and lower amounts of energy procedure. In practice, it appears that the surgical tip of the present invention pulls matter to be pulverized on a continuum basis and is not restricted by matter occlusion within the cannula that can lead to vast temperature fluctuations, spikes and deleterious consequences. Instead, the surgical tip of the present invention works with even with a partial occlusion created condition that degrades the matter as it travels along the lumen surface.

In the present invention, a repetitive pattern is etched into the inner surface of the lumen wall in a controlled pattern that follows Fourier's theorem. In a preferred embodiment micro-channels are patterned into the inner surface of the lumen wall in a helical configuration. However, any etched pattern may be utilized which is aligned in harmonic phase with the ultrasonic generated wavefront will reduce interference and accordingly increase the efficacy of the surgical tip while reducing deleterious effect. By way of example and in no way limiting, the etched pattern may be hyperbolic, parabolic or concentric circles which run the axial length of the lumen. In a preferred embodiment that will be discussed in detail herein, micro-channels are etched into the inner surface of the lumen wall in a helical pattern. More specifically, a triple helix pattern is etched into the inner lumen surface with one complete revolution occurring from the distal end point 20 to the hub base 24. The utilization of micro-grooves in a helical pattern establishes a resonance condition which is in phase with the frequency of the ultrasonic energy source. The resonance condition or "constructive interference" occurs when two waves are phase corresponding to 2Π, 4Π, etc.

The principle behind the function of the surgical tip of the present invention is based upon Fourier's theorem which may alternatively be termed the Fourier Transform or Fourier Series. Fourier's theorem teaches that any arbitrary periodic wave can be constructed by the superposition of a sufficiently large number of sinusoidal harmonic waves. Fourier's theorem may be represented as:

$$F(t) = \sum_{n=0}^{\infty} [A_n \operatorname{Sin} 2\pi F_n t + B_n \operatorname{Cos} 2\pi F_n t]$$

The following discussion is based largely upon, Hans C. Ohanian, Physics, 424–430 (W. W. Norton & Co. 1989) the disclosure of which is incorporated herein by reference. If the phase difference δ between two waves is zero, the two waves are said to be in phase. That is, the waves meet crest to crest and trough to trough, reinforcing each other. This condition is termed constructive interference. Put another way, constructive interference refers to the phenomenon in which the phases of waves arriving at a specified point over two or more paths of different length are such that the square of the resultant amplitude is greater than the sum of the squares of the component amplitudes.

If, however, the phase difference is ⊖=τ radians, or 180°, the two waves are said to be out of phase (they meet crest to trough) thereby canceling each other completely. This phenomenon is destructive interference.

Specifically, constructive interference occurs when the two waves are in phase corresponding to 2Π, 4Π, etc. which may be generally referred to as a harmonic progression. A harmonic progression refers to a sequence of numbers whose reciprocals form an arithmetic progression. In the present instance, this harmonic progression produces a focusing of the wavefront that centers in the lumen and transfers less energy toward the peripheral wall. It is noted that this is not established terminology, rather an acronym to aid in discussion. When phacoemulsification of lens nuclei tissue is performed within the confines of the surgical tip lumen, as opposed to a typical needle in which phaco generally occurs outside the lumen at the distal tip, endothelium is preserved.

Conversely, destructive interference occurs when two waves are 180° out of phase corresponding to Π, 3Π, 5Π, etc.

Figure 13:
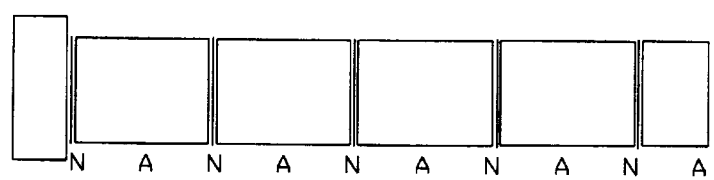
FIG. 13 is a schematic representation illustrating node and anti-node vibrational patterns.

Sound, including ultrasound, is produced in standing waves, which consist of nodes and antinodes. A wavefront can be defined as a surface of constant phase. Nodes are points of no motion, and antinodes are points of maximum motion. Put another way, nodes are the minima of standing waves and antinodes are the maxima. In the present invention, it is desired to establish a resonant condition at the surgical tip. Often, it is advantageous to utilize a pictoral representation or "waveform" to aid in the discussion of the form or shape of a wave. As illustrated by FIG. 13, in order to establish this resonant condition an anti-node must be created at the open end of the lumen. In FIG. 13, "A" represents the antinode with "N" representing a node.

Figure 10:
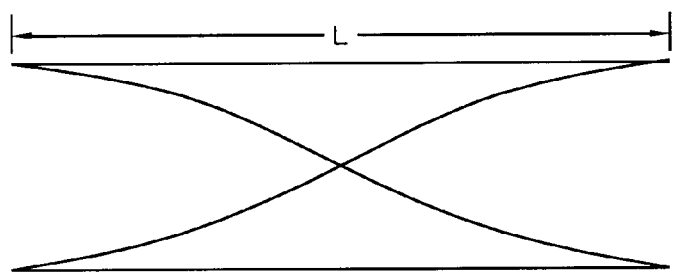
FIGS. 10, 11, and 12 are graphical illustrations of various waveforms associated with the behaviors of ultrasound frequencies of which will aid in the explanation thereof.

In the present invention, as illustrated in FIG. 10, the first harmonic has two nodes on the end and one antinode in the middle.

FIG. 10 represents the $1^{st}$ harmonic wherein:

$$\lambda_1 = 2L$$
$$F_1 = \frac{v}{\lambda_1} = \frac{v}{2}L$$
$$F_2 = \frac{v}{L} = 2F_1$$
$$\lambda_2 = L$$

Figure 11:
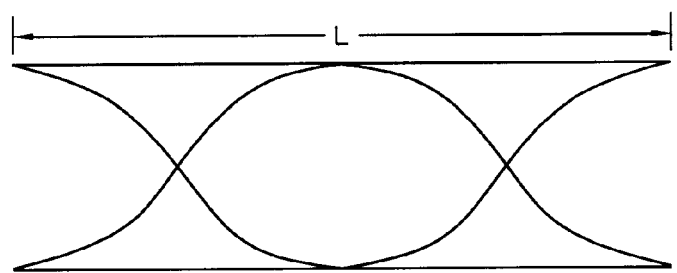
Figure 12:
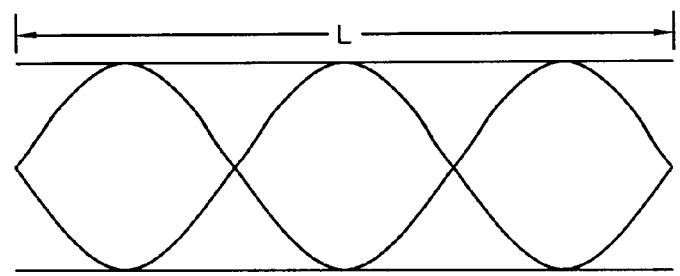

Similarly, FIG. 11 represents the $2^{nd}$ harmonic wherein:
Lastly, FIG. 12 represents the $3^{rd}$ harmonic wherein:

$$\lambda_3 = 2/3L$$
$$F_3 = \frac{2v}{2L} = 3F_1$$

Figure 14:
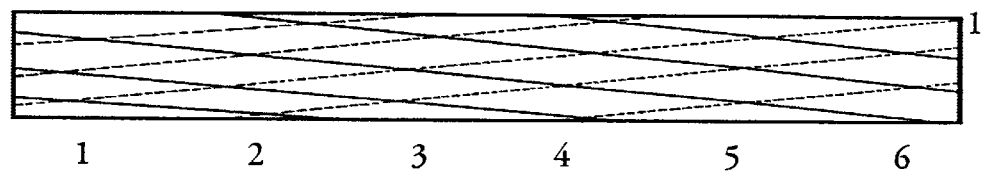
FIG. 14 illustrates an expanded view of a surgical tip in accordance with the present invention opened to a flat dimensional surface view wherein the helical grooves are set on a $2^{nd}$ harmonic.
Figure 18A:
FIG. 18a is a detailed view illustrating the width and depth of the channel shown in FIG. 18.
Figure 18:
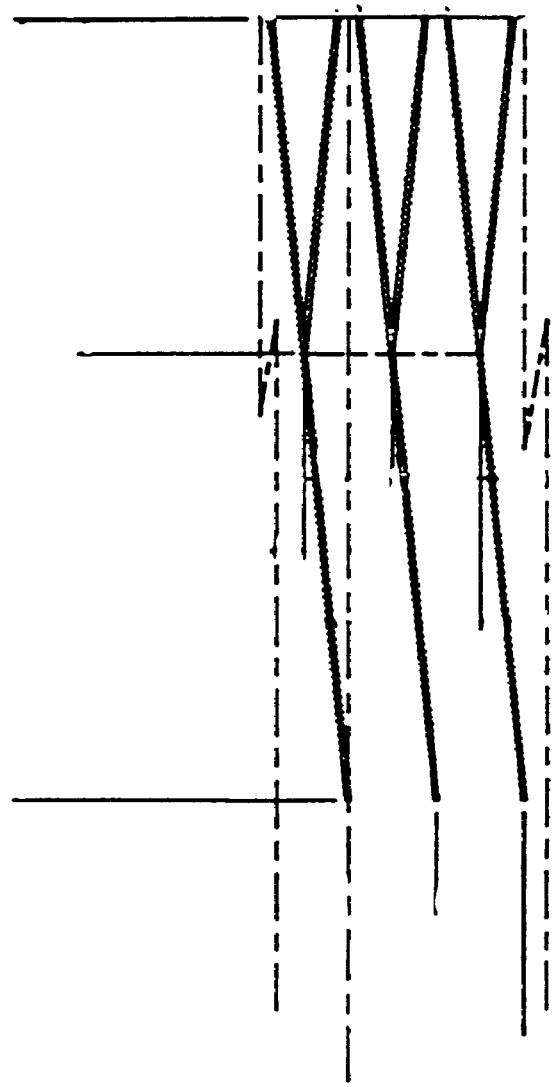
FIG. 18 is a circumferential view of the inner diameter of the surgical tip showing channels etched at a pitch of 1 revolution/30 mm.
Figure 19A:
FIG. 19a is a detailed view illustrating the width and depth of the channel shown in FIG. 18.
Figure 19:
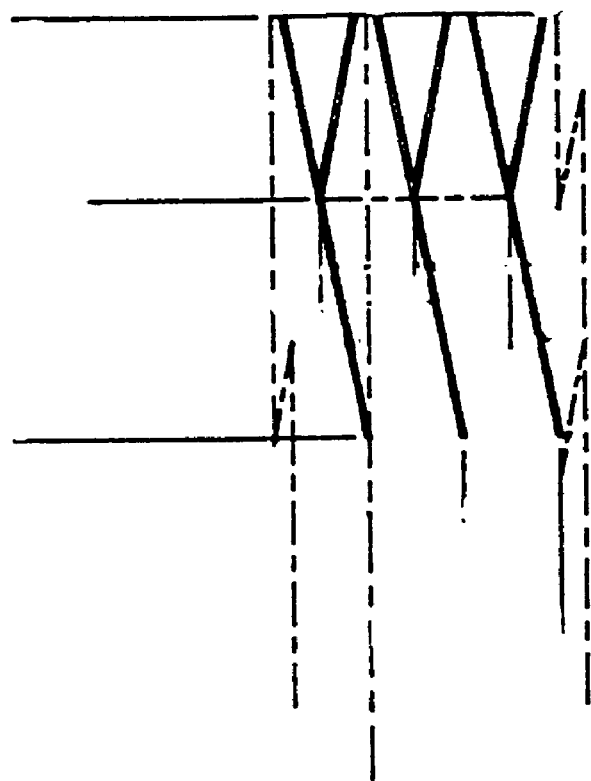
FIG. 19 is a circumferential view of the inner diameter of the surgical tip showing channels etched at a pitch of 2 revolution/30 mm.

Based upon the above referenced harmonics, utilizing Fourier's Series, helical grooves may be etched in the inner surface of the lumen wall in such a configuration to create a constructive resonance with the ultrasonic energy source. By way of example, FIG. 14 represents an expanded view of a phaco tip lumen with the inner tube diameter opened to a flat dimensioned surface view, with the helical channels set on the $2^{nd}$ Harmonic, i.e. the initiation and termination point of each groove are equal at each diverse end point. As illustrated in FIGS. 14 and 18, the triple helical pattern is established with six (6) helical intersections set on a pitch of 1/L (length) to 1/W(width) rotation. As illustrated in FIG. 19, with the helical channels set on the $3^{rd}$ harmonic, a triple helical pattern is established with twelve (12) helical intersections set on a pitch of 1/L (length) rotation to 1/W (width) rotation.

DERIVATIVE EQUATION FOR DETERMINING LUMEN LENGTH

Since the ultrasound frequency of the piezoelectric crystals will be fixed for a certain procedure (i.e. 27 kHz for liposuction), the length of the lumen selected will be varied to establish resonance.

Wavelength is related to the length of the lumen as follows:

$$\lambda = \frac{2}{n}L$$

where L is the length of the lumen and η is an integer (i.e. 1, 2, 3 . . . ). In the present instance, the focus is the length of the lumen:

$$L = \frac{n}{2}\lambda$$

The wavelength is given as a function of velocity and frequency and expressed as:

$$\lambda = \frac{v}{f}$$

While the ultrasound frequency is fixed, the velocity is dependent on several variables. For example, velocity is affected by pressure changes and temperature changes. Under surgical conditions, the pressure will generally be atmospheric. Therefore, in the present instance the biggest variable on velocity will be temperature and that calculation may be expressed as follows:

$$v = 331\frac{m}{s}\sqrt{1 + \frac{T}{273}}$$

where temperature (T) is in degrees Celsius. Combining these equations, the derivative formula for determining the desired lumen length may be expressed as:

$$L = n(165.5)\frac{\sqrt{1 + \frac{T}{273}}}{f}$$

Therefore, based upon the above-referenced derivative equation, assuming a frequency of 38.5 kHz and a temperature of 22° C. room temperature, the lumen's length would have to be integer multiples of 4.12 mm. Therefore, practical lumen lengths could be 16.49 mm, 20.61 mm or 24.73 mm.

Similarly, assuming the temperature of the lumen is close to or at body temperature (37° C.), the lumen's length would be integer multiples of 4.48 mm. Therefore, practical lumen lengths could be 13.73 mm, 18.32 mm or 22.90 mm.

The resonance condition will stay fixed so long as the conditions such as temperature and the density of the air remain relatively constant. As evidenced by the above calculations, over the temperature range of 22°–37° C., the length of the lumen changes approximately 2%. For purposes of this discussion it is assumed that the surgeon utilizes the surgical tip to cut or excise tissue, removes the tissue via vacuum and then resumes cutting. Therefore, the density of the air should be fixed over the course of the operation.

Results of Comparison Tests

Figure 20:
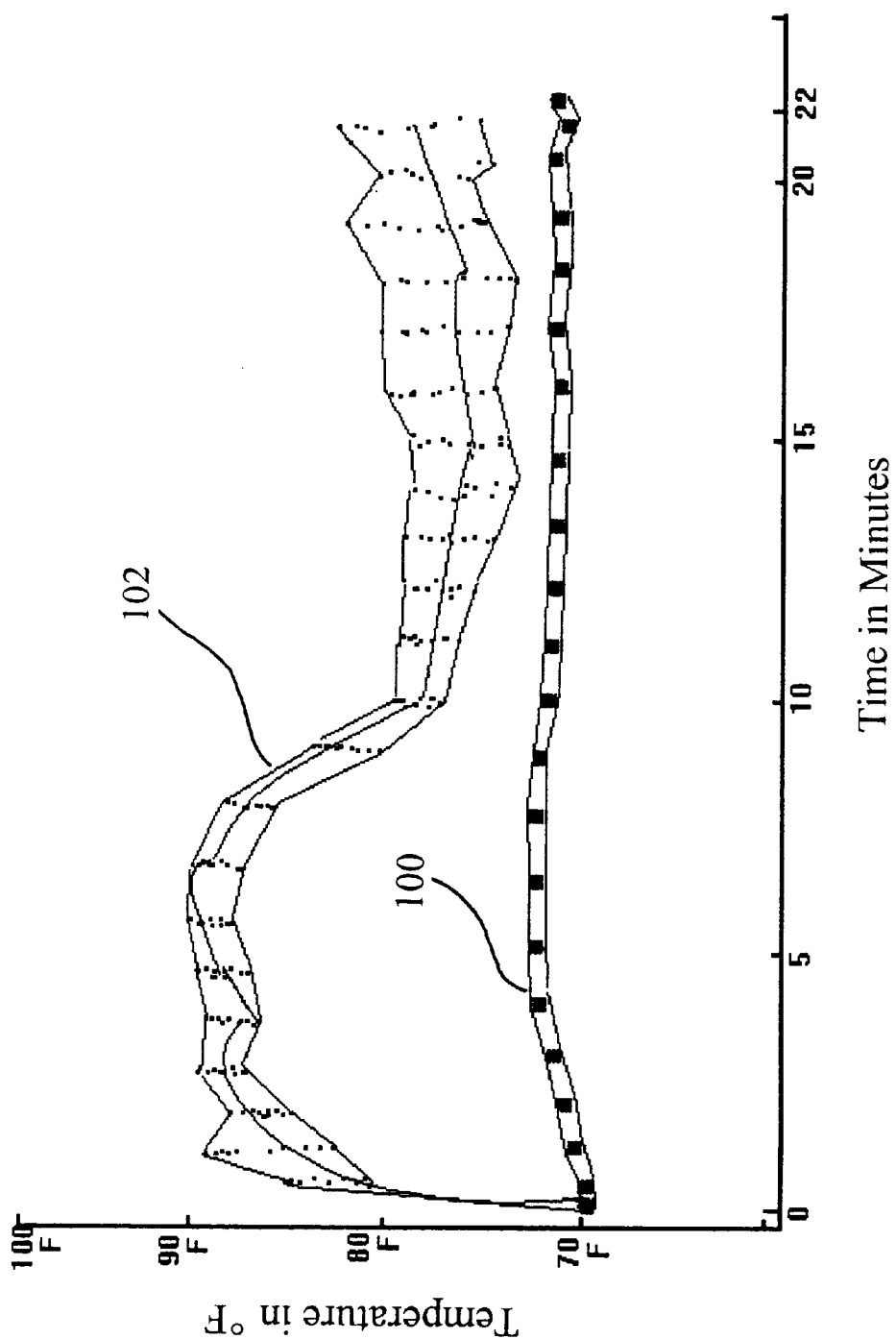
FIG. 20 is a graphical representation of the relative tip temperatures of a surgical tip of the present invention and a prior art industry standard phacoemulsification tip.

FIG. 20 graphically illustrates the reduced incidence of temperature spikes utilizing a surgical tip of the present invention. Comparison lab test were conducted using a surgical tip with a 45° bevel modified according to the present invention (FIG. 17) versus the same commercially available phacoemulsification tip having a 45° bevel without patterning on the inner lumen surface. The sample size for the test was ten (10) new needles of each type. The fluid temperature during the simulated phacoemulsification was 70° F. with the ambient room temperature also 70° F. The comparison trial was run for twenty-two (22) minutes at 50% power. As illustrated graphically in FIG. 20, Group I representing the surgical tip of the present invention 100 yielded consistently close temperature readings while Group II representing a commercially available phacoemulsification tip without inner lumen surface patterning 102 exhibited standard deviation temperature variance at each one (1) minute interval.

Specifically, controlled comparison lab tests were run 1:1 utilizing ten (10) needles modified in accordance with the present invention (Group I) and ten (10) commercially available phacoemulsification tips without patterning on the inner surface lumen. Other than the presence or absence of patterning on the inner lumen surface the tests were conducted utilizing the same components, phacoemulsification energy and needles of the same size and construct. When the resultant test data was plotted, FIG. 20 illustrates a temperature variance of approximately 20 degrees F between Group 1 (100) and Group II (102) over the first ten minutes of run time and approximately 10 degrees F between for two test groups for the second ten minutes of run time. The twenty minute run time approximates the average fifteen (15) uses (cataract case procedures) for a phacoemulsification needle.

Group I invention group (S=10) yielded consistently close temperature readings, i.e. <1.5 degrees F at each one (1) minute interval for twenty (20) minutes and maintained a 3 degree F temperature increase difference off of start time base line during the test schedule. Group II (S=10) had a standard deviation temperature variance of 6.32 degree F between individual cell groupings at each one (1) minute interval for the first ten (10) minutes and a 7.4 degree F standard deviation temperature variance between individual cell groupings for the $2^{nd}$ ten (10) minutes of the test run time from the start base line of 70° F.

Figure 21:
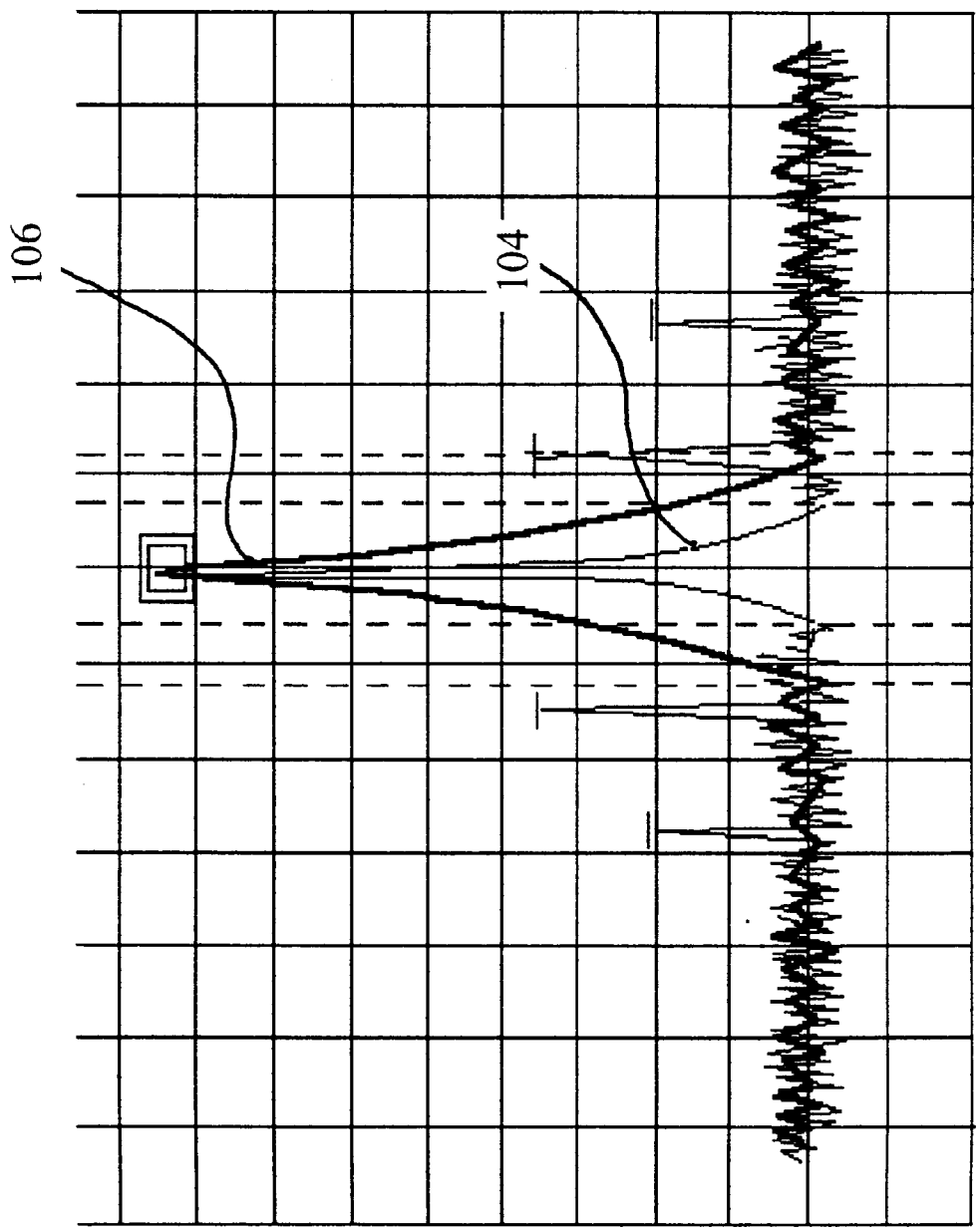
FIG. 21 is a superimposed spectrum analysis of 1:1 comparison of a surgical tip of the present invention and a prior art industry standard phacoemulsification tip.

FIG. 21 is a superimposed spectrum analysis of a 1:1 comparison of a surgical tip modified in accordance with the present invention 104 (Group I) and a the same phacoemulsification needle without patterning on the inner lumen surface 106 (Group II). The test was conducted at 50% phaco power linear.

Figure 22:
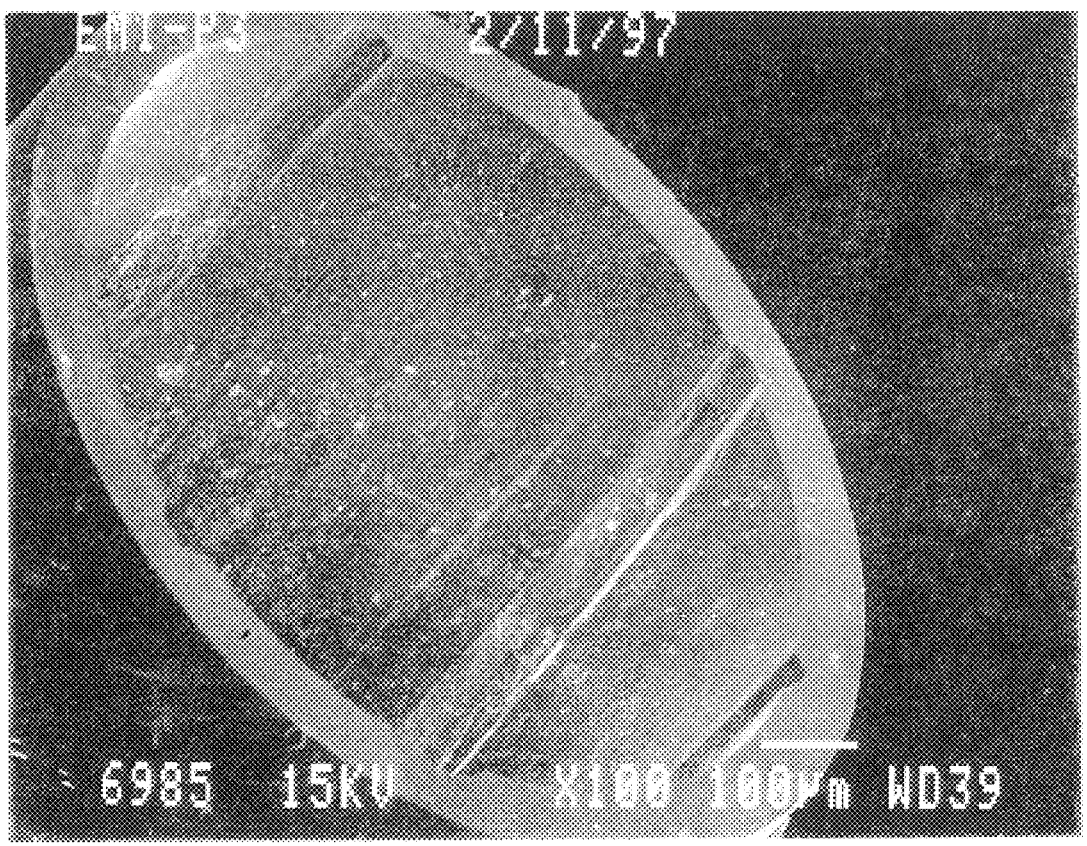
FIG. 22 is a scanning electron microscope image of a surgical tip of the present invention at ×100 magnification illustrating distal leading edge geometry curve.
Figure 23:
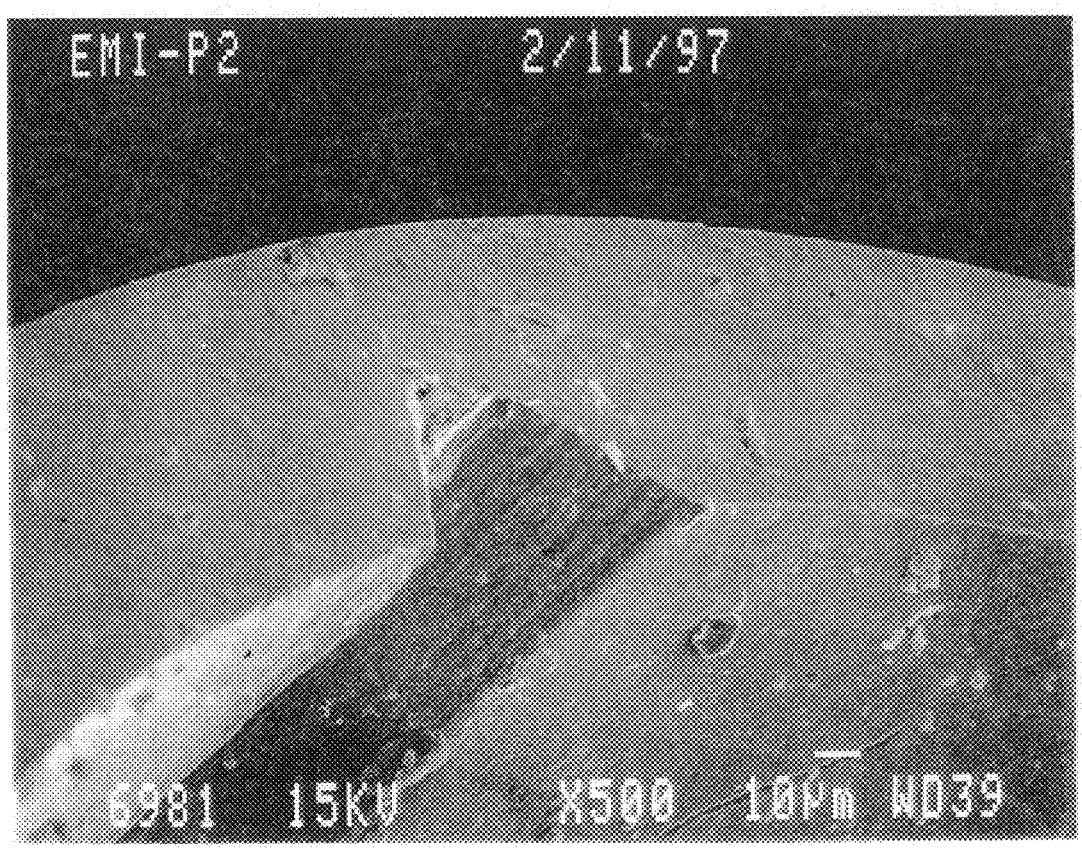
FIG. 23 is a scanning electron microscope image of a used surgical tip of the present invention at ×500 magnification.

Group I:
39.995 kHz Center Frequency–0.730 kHz Power Band ¦20 bdV Magnitude Power=Y 2 Sidebands/ ½ & ⅓ Power
17.19 dbV & 9.97 dbV Magnitude Group II:
39.995 kHz Center Frequency–1.39 kHz Power Band ¦ 20 bdV Magnitude Power=Y As discussed above, striations and defects in the peripheral edge and inner surface of the lumen can greatly effect the efficiency and heat build-up associated with phacoemulsification tips. FIG. 22 is a scanning electron microscope image of a surgical tip modified in accordance with the present invention at ×100 magnification illustrating distal leading edge geometry curve. The distal end of the surgical tip is clear of cupping impressions and manufacturing deformation. Similarly, FIG. 23 is a scanning electron microscope image of a used surgical tip modified in accordance with the present invention at ×500 magnification. Although this tip has been used fifteen (15) times, the distal end of the surgical tip is free from metal deformation and striations as usually seen from high power waveform propagation.

Figure 24:
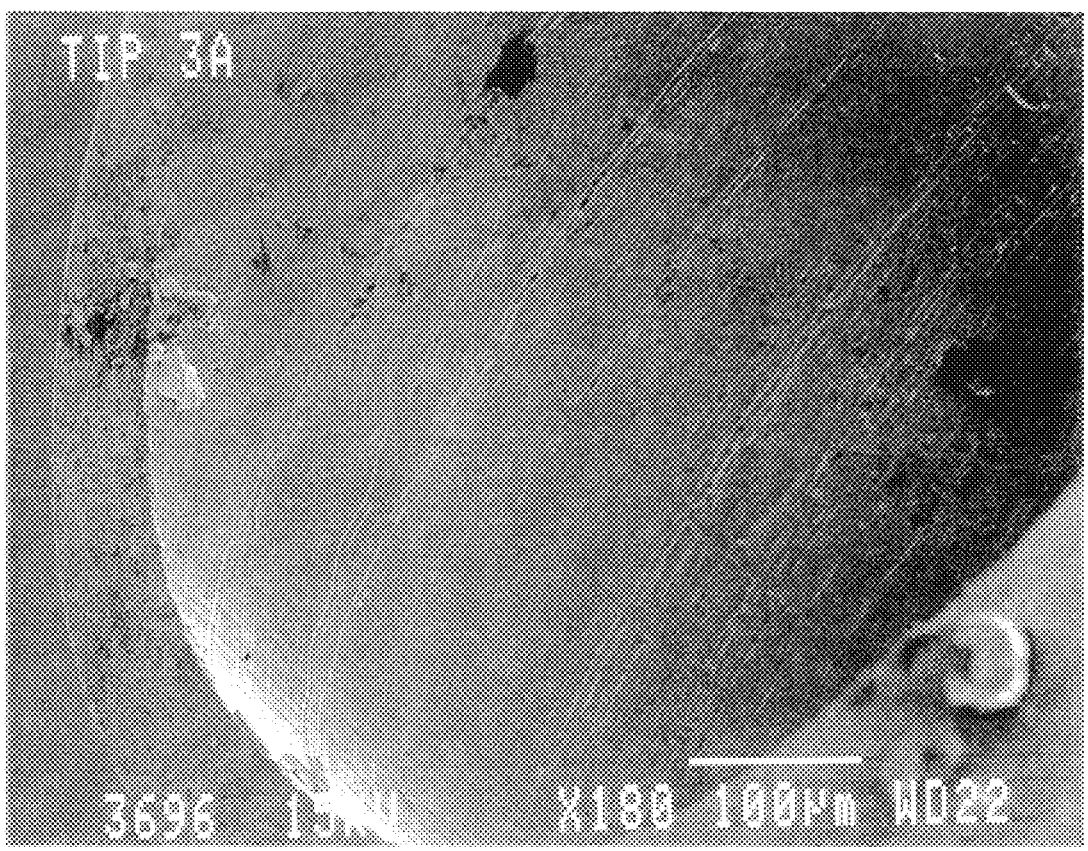
FIG. 24 is a scanning electron microscope image of a used prior art phacoemulsification needle at ×180 magnification illustrating multiple striation on the lumen surface from wave propagation.
Figure 25:
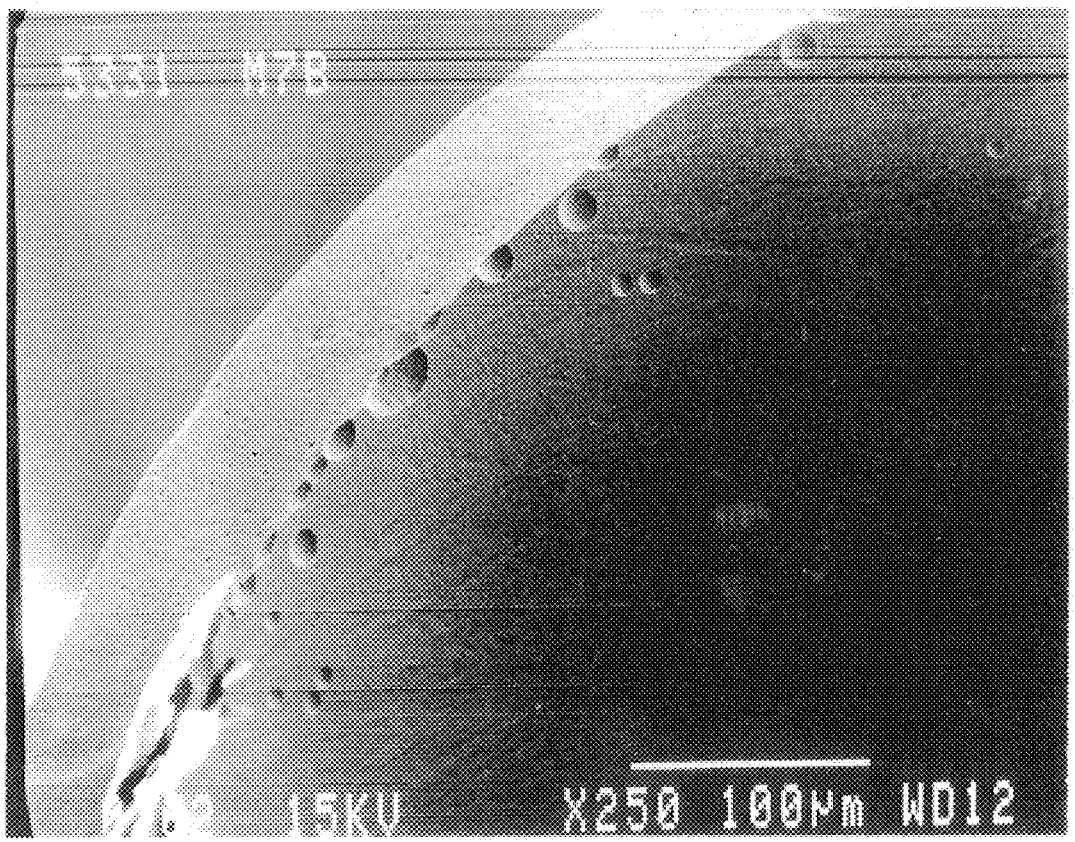
FIG. 25 is a scanning electron microscope image of a used prior art phacoemulsification needle at ×250 magnification illustrating cupping impressions left in the lumen surface by waveform energy.
Figure 26:
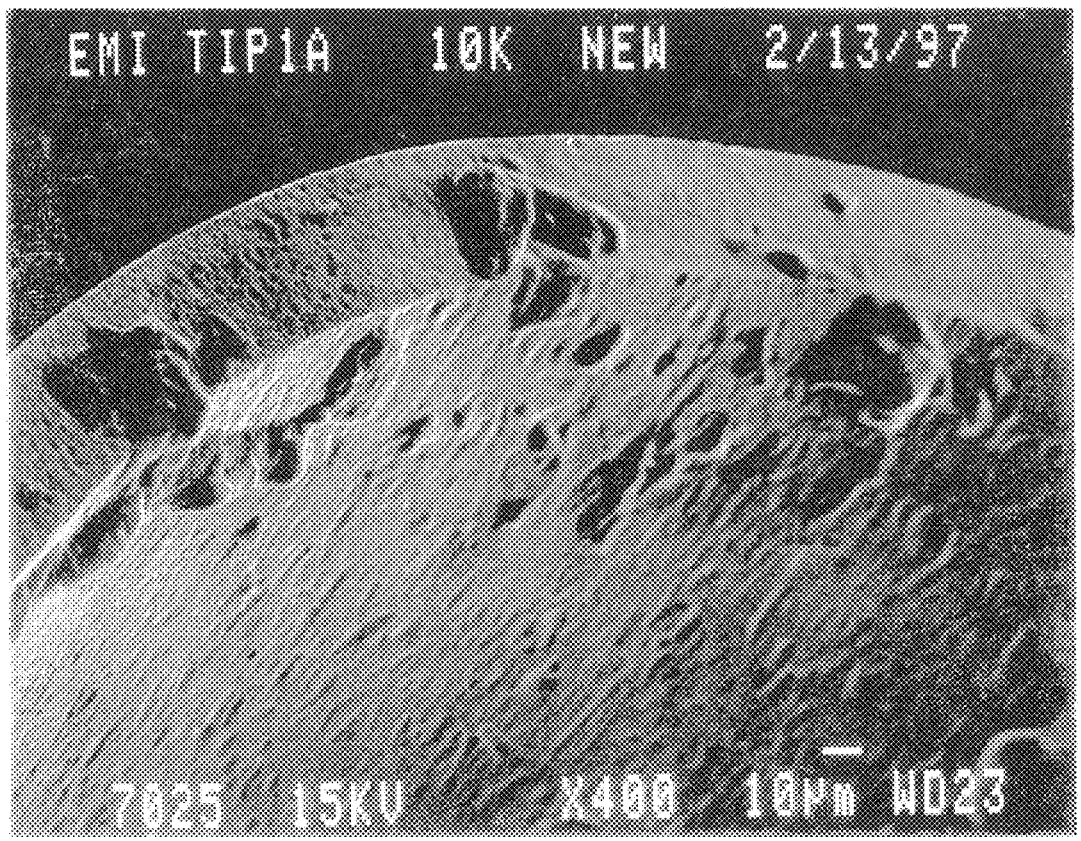
FIG. 26 is a scanning electron microscope image of a new phacoemulsification needle (prior art) at ×400 magnification illustrating axial length striations.

In contrast, FIG. 24 is a scanning electron microscope image of a prior art phacoemulsification needle, after having been used fifteen (15) times at ×180 magnification illustrating multiple striation on the lumen surface from wave propagation. Similarly, FIG. 25 is a scanning electron microscope image of a prior art phacoemulsification needle used ten (10) times at ×250 magnification illustrating cupping impressions left in the lumen surface by waveform energy during use. These cupping impressions substantially reduce efficiency and increase the likelihood of heat build-up at the distal end. FIG. 26 is a scanning electron microscope image of a new prior art phacoemulsification needle at ×400 magnification illustrating axial length striations which can lead to waveform energy destructive interference during use producing heat build-up and cannula inefficiency.

The micro-grooving of the surgical tip of the present invention will now be discussed in greater detail.

MICRO-POLISHING TECHNIQUE

Prior to etching the inner surface of the lumen, the surgical tip must undergo micro-polishing. There are several commercially available and recognized techniques for micro-polishing. In a first micro-polishing technique, a thin gold wire is inserted into the lumen of the surgical tip. This gold wire may be 0.8–1.1 mm depending upon the inner diameter of the surgical tip. The thin gold wire is secured by a collet or broach that is grounded. An AC current having a high voltage of approximately 220V having a low amperage of 5 amps. is introduced to the wire thereby initiating ion alignment on the lumen wall.

In a second micro-polishing technique, which may be utilized for both the lumen surface and the distal end peripheral edge, a combination of silica/alumina slurry that is air compressed is introduced through the lumen after a silicon plug is inserted in the distal end of the lumen to prevent lumen entry of the slurry mix. The result is a highly polished mirror finish with a sharp linear clear edge which preferably has no deviations on the plane surface geometry.

MICRO-CHANNELING OF LUMEN

In the preferred embodiment, a pattern of six micro-channels is mechanically etched into the internal surface of the surgical tip. More preferably, these micro-channels are spaced and patterned to form a triple helix on the internal surface of the surgical needle. While a triple helical pattern is preferred, any helical pattern may be utilized which results in a resonance condition being established with the ultrasonic source.

Figure 15:
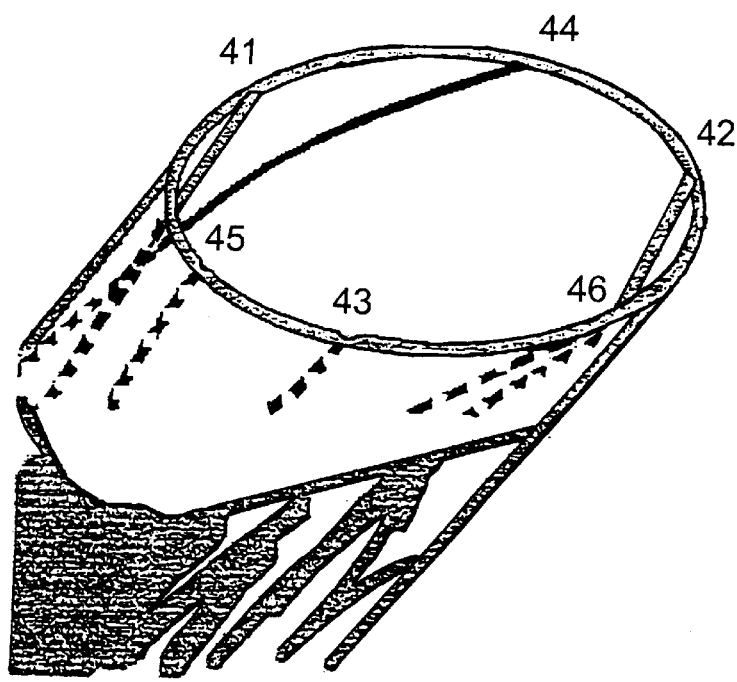
FIG. 15 illustrates a perspective view of the distal end of the surgical tip showing a preferred channel orientation.

With reference to the preferred embodiment, FIG. 15 illustrates three equally spaced channels 44, 45 and 46 are cut in a clockwise rotational direction with an additional three equally spaced channels 41, 42 and 43 cut in a counter-clockwise direction.

With reference to FIG. 27, the cutting tool 50 used to mechanically etch the internal channel may be ground from a standard ⅛" round carbide tool blank. In this instance, carbide is preferred due to its stiffness, however, any appropriate material known in the tooling industry may be utilized. Additionally, the stiffness of carbide is desired to aid in imparting the desired rotational cuts since the tool is sensitive to rotational loading based upon the small cross-section of the tool.

As illustrated in FIGS. 27 and 28, the micro cutting tool is designed to be pushed inside the surgical tip lumen and contains three equally spaced cutting edges 52, 54 and 56. Preferably, the cutting edges are spaced at 120° intervals. More specifically, the micro-tool may be an equilaterally opposed rod with the peripheral cutting edges pitched in a conical shape which is designed to be pushed or drawn through the lumen 18 secured to a broach or collet at a predetermined revolution relationship (e.g. pitch). As the tool is pushed through the central bore of the lumen of the surgical tip, each cutting edge etches a channel into the internal surface of the lumen wall. In use, the tool relies on the symmetry of the cutting edge to achieve a proper fit within the lumen and support the desired chip load. In use, the micro cutting tool is designed to etch channels of a desired depth on a single pass through the lumen.

In a preferred embodiment, each cutting edge is designed with a side relief to provide for the rotationally etched or cut channels needed. Preferably, the channels are etched with a rotational pitch of 12° degrees per millimeter, both clockwise and counterclockwise. This side relief is necessary to allow for the combined rotational and linear cut. The side relief may be oriented along both sides of the cutting edges so that one micro cutting tool may be utilized for both the clockwise and counter-clockwise cuts.

By way of example, and in no way intended to limit the manufacture of the surgical tip of the present invention, the etching may be accomplished utilizing a CNC lathe that has full C-axis capability. The C-axis capability allows for fine rotational positioning of the spindle and to position the spindle with respect to other programmable axis (e.g. the X and Z axis). The cutting tool may be mounted onto the cross-slide (not shown) of the lathe and the lumen clamped into the spindle (not shown) by an appropriate sized and shaped collet.

Figure 29:
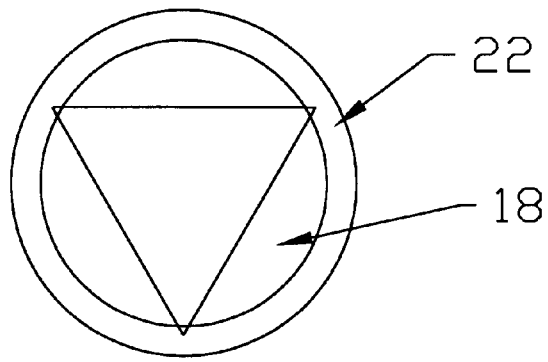
FIG. 29 is an end view illustrating a micro-tool being drawn clockwise through a lumen.
Figure 30:
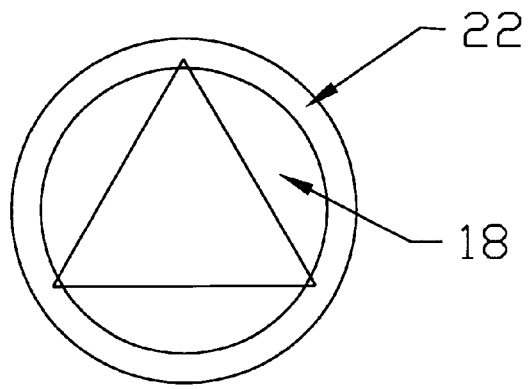
FIG. 30 is an end view illustrating a micro-tool being drawn counter-clockwise through a lumen.
Figure 31:
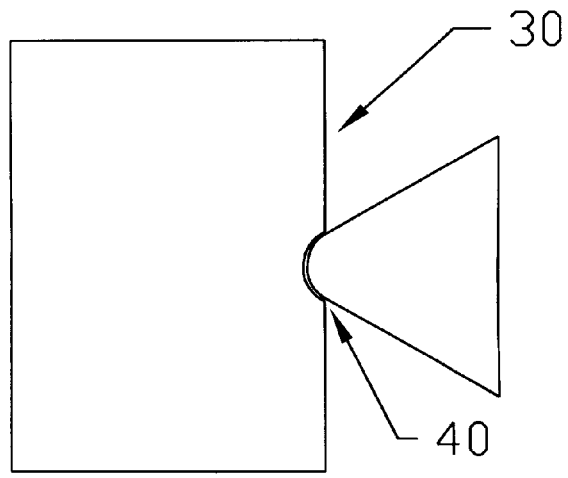
FIG. 31 is a cross-sectional view illustrating the etching pitch and depth of the microtool.

The CNC is also programmed to engage the micro-cutting tool and lumen, the spindle should be rotated slightly clockwise to provide the correct pitch angle. As illustrated in FIGS. 29 and 30, once the micro-tool travels the length of the lumen is then retracted by rotating the spindle in the opposite direction. As the micro-tool is retracted it follows the channels just etched in the inner diameter of the lumen. The micro-tool is then introduced through the lumen with the spindle rotated counter-clockwise and withdrawn in the same manner.

As the lumen is cut or etched, a metal "chip" is generated and pushed down the lumen. As the micro-tool is retracted the chip remains in the lumen. The chip may be removed by manually pushing a gage pin down the lumen of the surgical tip and ejecting the chip.

A final silica/alumina slurry is passed through the lumen surface to polish both the channels and the lumen surface and leave all surface geometry with clear linear edges.

Preferably, the micro channels are from $1/10^{th}$ to $1/3^{rd}$ of the wall thickness and are preferably pitched at 0.333 of an arch of a circle.

The method of channeling or scoring the inner surface diameter of the lumen as described above constitutes an inventive method in addition to the surgical tip itself.

Figure 16:
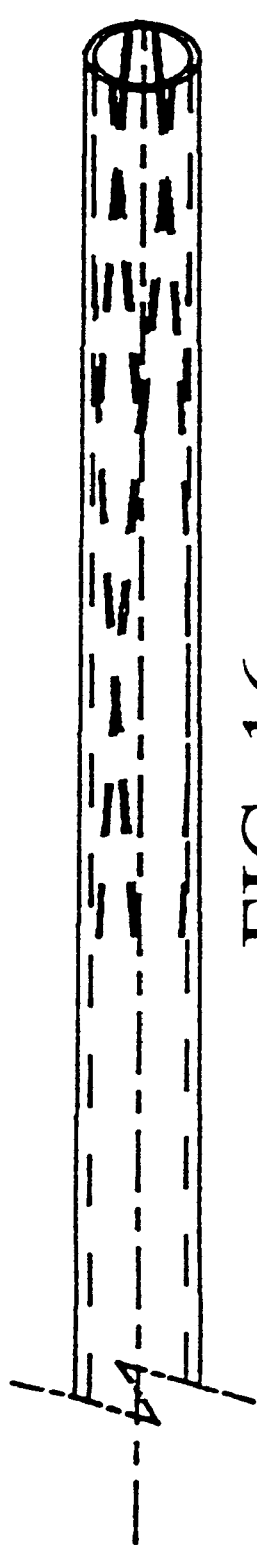
FIG. 16 illustrates a distal end elevational view showing diverging channels.

FIG. 16 illustrates time angled edges with diverging channels having an antinode established at the distal end of the lumen.

Figure 17:
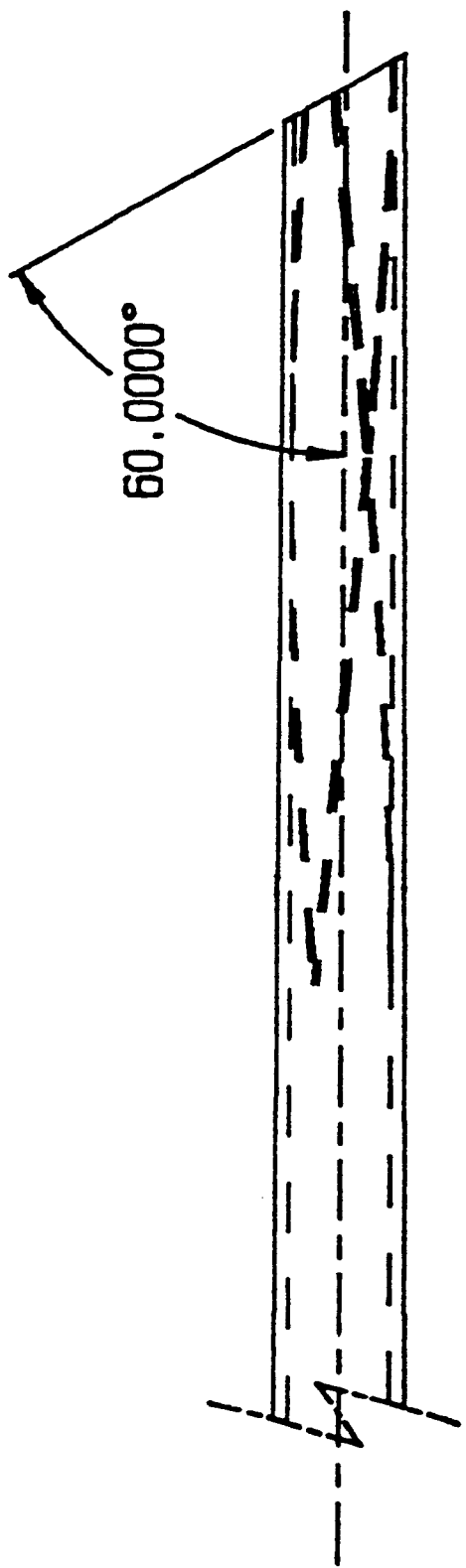
FIG. 17. is a side view of the surgical needle of the present invention illustrating an alternative 60° pitched distal tip.

FIG. 17 is a side view of the surgical tip of the present invention illustrating an alternative 60° pitched distal tip.

FIG. 18 is a circumferential view of the surgical tip of the present invention illustrating the channel detail. The pitch is equal to 1 revolution/30 mm of length of the lumen.

The previously described embodiments of the present invention have many advantages over the prior art, including but not limited to improved fluidics and the reduction or dampening of harmonics attendant with the ultrasonic frequencies utilized in phacoemulsification.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A surgical tip for the emulsification of tissue, for connection to an energy source generating a wavefront, comprising in combination:

an elongate hollow member including a wall defining a lumen said elongate hollow member further having a proximal end and an invasive distal end thereby defining an axial length;

means for connecting said proximal end of said elongate hollow member in fluid communication with the energy source thereby allowing the wavefront to travel through said lumen; and an etched pattern positioned on said lumen further comprising micro-channels aligned in a helical configuration.

2. A surgical tip as in claim 1, wherein said micro-channels are aligned in a double helix configuration.

3. A surgical tip as in claim 1, wherein said micro-channels are aligned in a triple helix configuration.

4. A surgical tip as in claim 1, wherein said micro-channels extend the axial length of said elongate hollow member.

5. A surgical tip as in claim 1, wherein said helical configuration is at a pitch of one revolution per 30 mm in axial length.

6. A surgical tip as in claim 1, wherein said helical configuration is at a pitch of two revolutions per 30 mm in axial length.

7. A surgical tip for the emulsification of tissue, for connection to an energy source generating a wavefront, comprising in combination:

an elongate hollow member including a wall defining a lumen said elongate hollow member further having a proximal end and an invasive distal end;

means for connecting said proximal end of said elongate hollow member in fluid communication with an energy source thereby allowing a wavefront to travel through said lumen; and at least one micro-channel positioned on-said lumen, wherein said micro-channel has a helical pattern.

8. The surgical tip according to claim 7, wherein said micro-channel makes an integer number of complete revolutions from the distal end to proximate to the proximal end.

9. A surgical tip for the emulsification of tissue, for connection to an energy source generating a wavefront, comprising in combination:

an elongate hollow member including a wall defining a lumen said elongate hollow member further having a proximal end and an invasive distal end;

means for connecting said proximal end of said elongate hollow member in fluid communication with an energy source thereby allowing a wavefront to travel through said lumen; and six micro-channels-positioned on said lumen, each having a helical pattern, such that a first three of the six micro-channels are equally spaced and are in a clockwise rotational direction with respect to the distal end and a second three of the six micro-channels are equally spaced and are in a counter clockwise rotational direction with respect to the distal end, and wherein the starting position of the first three micro-channels with respect to the distal end and the starting position of the second three micro-channels with respect to the distal end are offset from each other such that the first three micro-channels intersect the second three micro-channels at a desired distance from the distal end.

10. The surgical tip according to claim 9, wherein the offset is approximately 60 degrees.

11. The surgical tip according to claim 9, wherein said counter-clockwise rotational helical micro-channels are positioned to intersect with the clockwise rotational helical micro-channels at ½ (offset/pitch) from the distal end, wherein offset is expressed in units of degrees and pitch is the pitch of the micro-channels expressed in units of degrees per unit length.

12. A method for emulsifying tissue, said method comprising the following steps:

(a) providing a surgical tip for the emulsification of tissue, comprising:
an elongate hollow member including a wall defining a lumen, said elongate hollow member further having a proximal end and a distal end; and
means for connecting said proximal end of said elongate hollow member in fluid communication with an energy source;

(b) applying suction to the surgical tip such that tissue proximate the distal end can be suctioned into the surgical tip; and (c) positioning the distal end near tissue to be emulsified, wherein at least one micro-channel is positioned on said wall, wherein said micro-channel has a helical pattern.

* * * * *

UNITED STATES PATENT AND TRADEMARK OFFICE
CERTIFICATE OF CORRECTION

PATENT NO.   : 6,283,974 B1
DATED        : September 4, 2001
INVENTOR(S)  : Aaron James Alexander It is certified that error appears in the above-identified patent and that said Letters Patent is hereby corrected as shown below:

Column 10,
Line 35, "$\ominus=\tau$" should read -- $\delta=\pi$ --

Column 13,
Line 32, "Power" should read -- Power -- --.

Column 16,
Line 29, "on-said" should read -- on said --.

Column 18,
Lines 5-6, "positioned on said wall" should read -- positioned on an inside surface of said wall --.

Signed and Sealed this

Second Day of April, 2002

Attest:

JAMES E. ROGAN
*Attesting Officer*    *Director of the United States Patent and Trademark Office*